United States Patent

Nakaso et al.

[11] Patent Number: 5,796,004
[45] Date of Patent: Aug. 18, 1998

[54] METHOD AND APPARATUS FOR EXCITING BULK ACOUSTIC WAVE

[75] Inventors: Noritaka Nakaso; Yusuke Tsukahara, both of Tokyo, Japan

[73] Assignee: Toppan Printing Co., Ltd., Tokyo, Japan

[21] Appl. No.: 736,424

[22] Filed: Oct. 24, 1996

[30] Foreign Application Priority Data

Oct. 24, 1995 [JP] Japan .................. 7-274609
Jul. 9, 1996 [JP] Japan .................. 8-179483

[51] Int. Cl.$^6$ .................................. G01N 29/04
[52] U.S. Cl. .................. 73/643; 73/632; 73/655; 73/657
[58] Field of Search .................. 73/632, 643, 655, 73/657, 606, 603, 601, 649

[56] References Cited

U.S. PATENT DOCUMENTS 3,506,327  4/1970  Leith et al. .................. 73/596
3,978,713  9/1976  Penney .................. 73/643
4,541,280  9/1985  Cielo et al. .
4,581,939  4/1986  Takahashi .................. 73/647
4,683,750  8/1987  Kino et al. .................. 73/606

FOREIGN PATENT DOCUMENTS 6-186208  7/1994  Japan .

*Primary Examiner*—Hezron E. Williams
*Assistant Examiner*—Nashmiya Fayyaz
*Attorney, Agent, or Firm*—Armstrong, Westerman, Hattori, McLeland & Naughton

[57] ABSTRACT

In a method and an apparatus for exciting acoustic waves, the surface of an object is irradiated with coherent parallel energy beams and coherent focusing energy beams which have different frequencies in such a manner that they overlap each other to generate interference fringes (concentric circles) propagating from outside to the inside at propagation speed which is higher than a specific acoustic speed of the object. The acoustic waves are excited in accordance with distortion distribution generated in the surface of the object attributable to the photo-thermal effect of the interference fringes, the acoustic waves being focused to a small region in the object, the position of which is determined by the specific acoustic speed of the object and the propagation speed of the interference fringes.

15 Claims, 13 Drawing Sheets

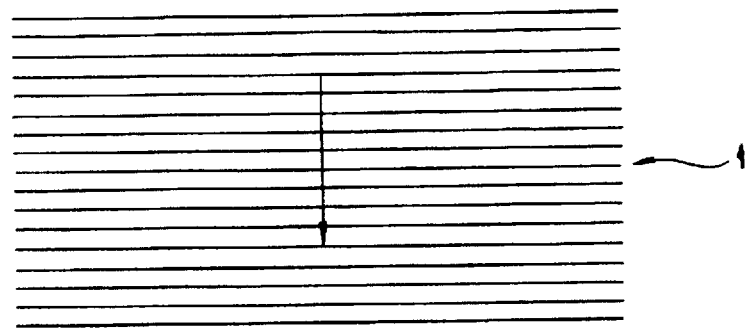
F I G. 1
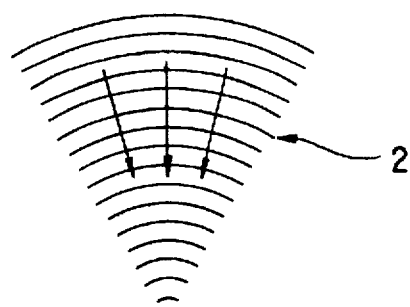
F I G. 2
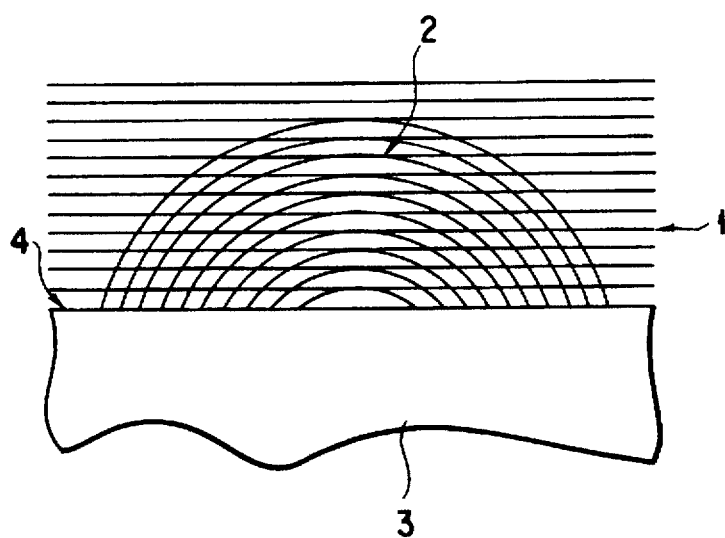
F I G. 3

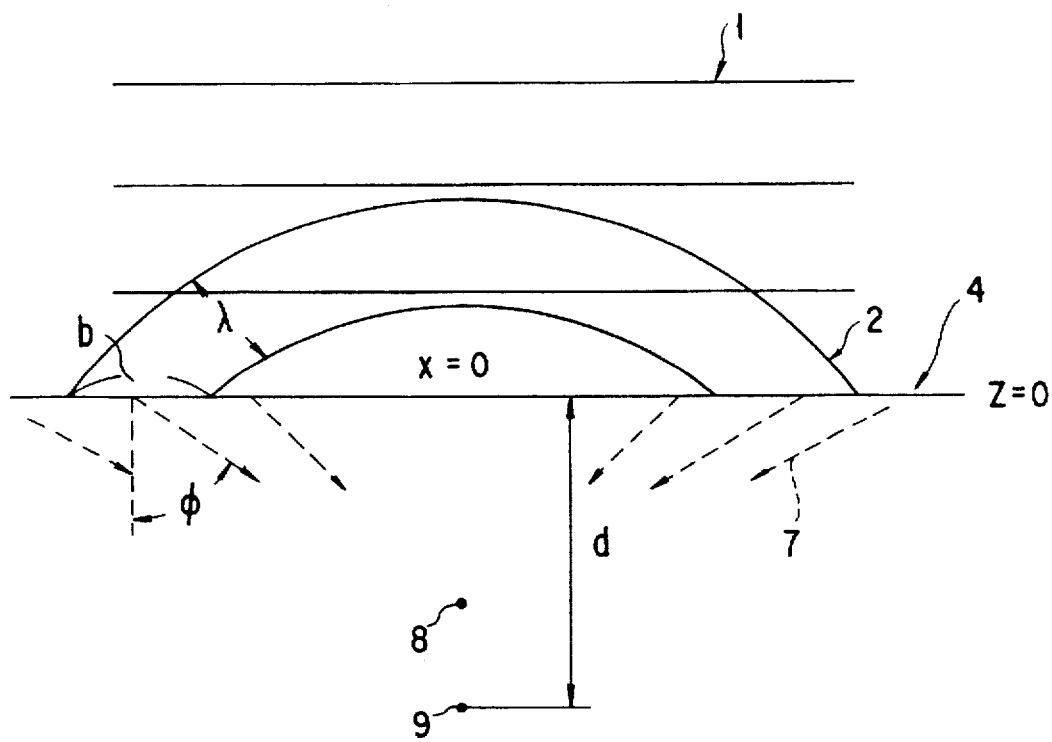
F I G. 5
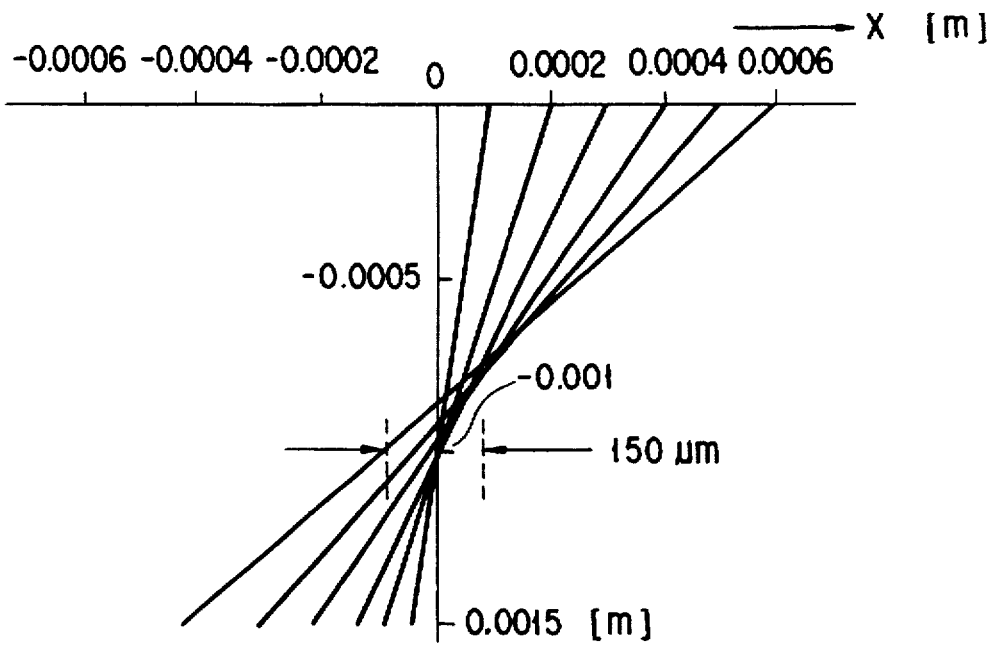
F I G. 6

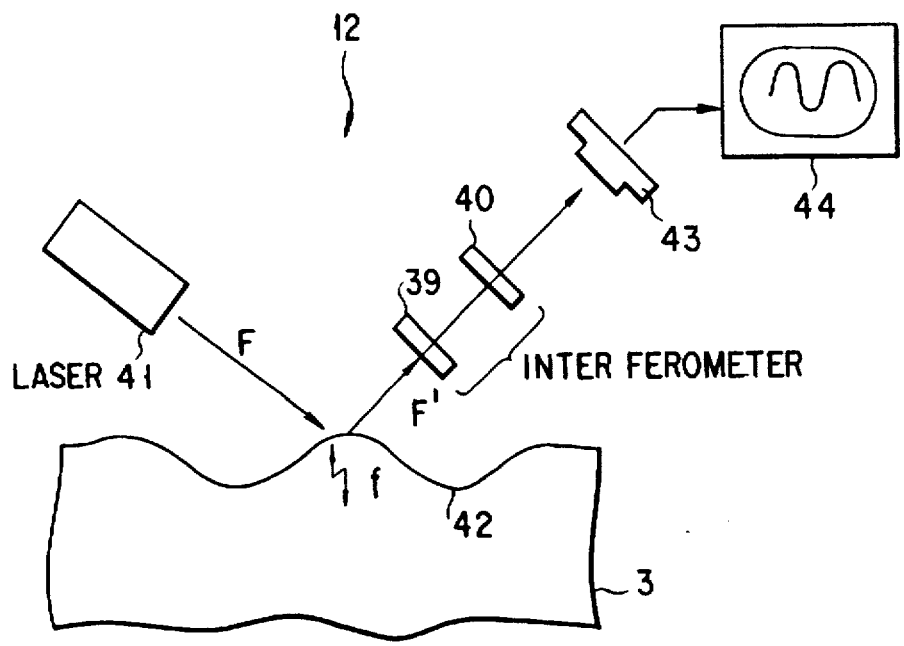
F I G. 19
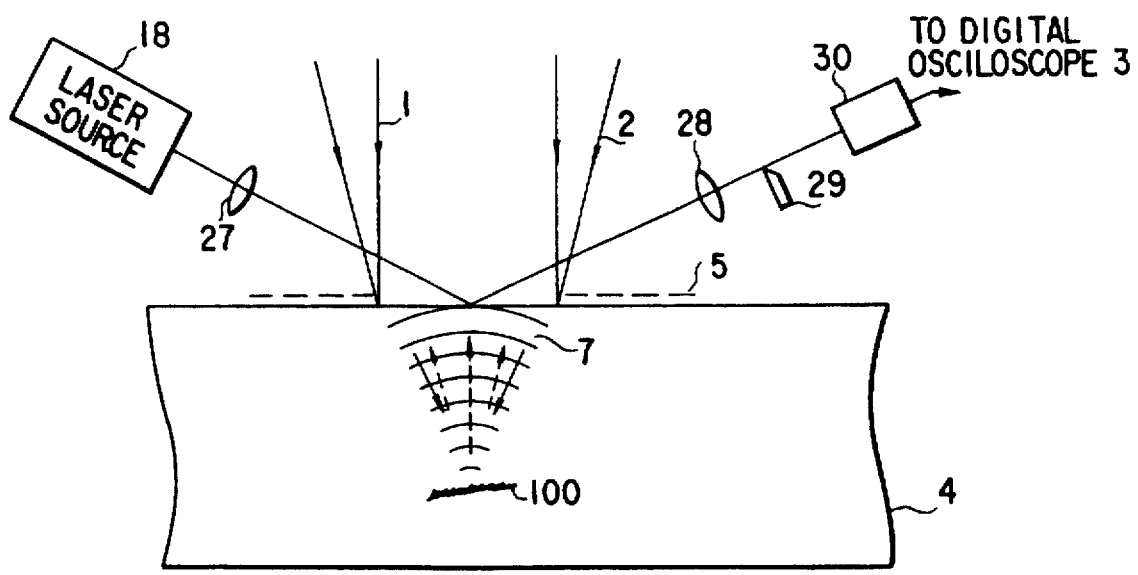
F I G. 20

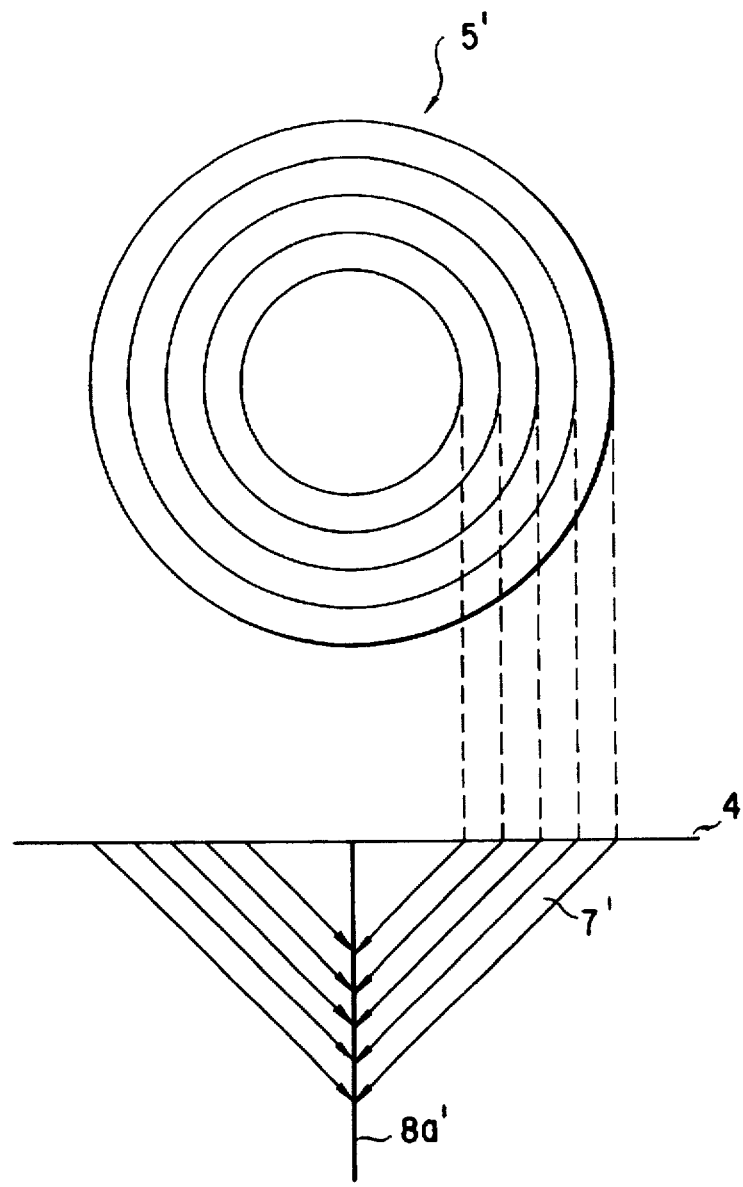
F I G. 21

5,796,004

METHOD AND APPARATUS FOR EXCITING BULK ACOUSTIC WAVE

BACKGROUND OF THE INVENTION

1. Field of the Invention

The present invention relates to a method and an apparatus for exciting bulk acoustic waves which are focused from the surface of an object toward an internal small region and to a method and an apparatus for evaluating a material by inspecting the characteristics of the material in the object in a non-contact and non-destructive manner by using the bulk acoustic waves.

2. Description of the Related Art

As a method of detecting small defects, such as small cracks in a ceramic, voids in an IC package and the like, which deteriorate the strength and reliability of a material or a structure, a method has been disclosed in Japanese Patent Laid-open Publication (KOKAI) No. 6-186208. According to this disclosure, the surface of an object is irradiated with two interference energy beams having frequencies slightly different from each other in such a manner that the two interference energy beams are caused to intersect above the object so as to form interference fringes to be scanned. The effect of the interference fringes is used to realize distortion distribution on the surface of the object, the distortion distribution having the same intervals as those of the interference fringes. Then, acoustic waves are radiated in a direction determined by the acoustic speed of acoustic waves propagating in the object or along the surface of the same and the scanning speed of the interference fringe. By detecting generated echo, the state in the object is inspected.

However, since the acoustic waves are parallel beams (a parallel wavefront propagates while maintaining the parallel state), the place in the object encountered a defect cannot be specified. That is, three-dimensional resolution is unsatisfactory. To form interference fringes on the surface of the object, laser beams having certain spot size must be used. However, the acoustic wave to be excited has an extension similar to that of the laser beam. As a result, even if a probe beam capable of focusing into a small region is used in the inspection operation, a satisfactorily high spatial resolution cannot be obtained. Thus, there arises a problem in that a small defect or the like in the material cannot accurately be detected.

On the other hand, a method has been disclosed in U.S. Pat. No. 4,541,280 (Cielo et al.) in which the surface acoustic waves are generated by laser beam that is focused onto a surface to irradiate it in an arcuate pattern as a partial annulus or as a still or moving fringe pattern having an equal pitch so as to inspect the surface of an object.

However, the foregoing method is structured to only excite surface acoustic wave which propagates along the surface of the object. Therefore, evaluation of the defect in a material and scanning of flaws in the same cannot be performed.

SUMMARY OF THE INVENTION

An object of the present invention is to provide a method and an apparatus capable of overcoming the above-mentioned problems and exciting bulk acoustic waves focusing to a small region in an object.

Another object of the present invention is to provide a method and an apparatus for evaluating a material in a non-contact and non-destructive manner with a structure such that the position to which acoustic waves are focused is three-dimensionally scanned to precisely evaluate a defect, the structure, and film thickness et al. of a small region in an object with high resolution.

According to the present invention, there is provided a method of exciting acoustic waves comprising the following steps of:

irradiating a surface of an object with coherent parallel energy beams and coherent focusing energy beams which have different frequencies such that the parallel energy beams and the focusing energy beams overlap each other to generate interference fringes in the form of concentric circles propagating from the periphery to the center of the object at propagation speed which is higher than a specific acoustic speed of the object; and exciting acoustic waves in accordance with a distortion distribution generated in the surface of the object attributable to a photo-thermal effect of the interference fringes, the acoustic waves being focused to a small region in the object, a position of which is determined by the specific acoustic speed of the object and the propagation speed of the interference fringes.

According to the present invention, there is provided a method of evaluating a material of an object, the method comprising the following steps of:

irradiating a surface of the object with coherent parallel energy beams and coherent focusing energy beams which have different frequencies such that the parallel energy beams and the focusing energy beams overlap each other to generate interference fringes in the form of concentric circles propagating from the periphery to the center of the object at propagation speed which is higher than a specific acoustic speed of the object;

exciting acoustic waves in accordance with a distortion distribution generated in the surface of the object attributable to a photo-thermal effect of the interference fringes, the acoustic waves being focused to a small region in the object, a position of which is determined by the specific acoustic speed of the object and the propagation speed of the interference fringes; and detecting the acoustic waves reflected by the small region or allowed to pass through the small region and then allowed to reach a front surface or a rear surface of the object with a probe beam so as to analyze characteristics of the material of the object.

According to the present invention, there is provided an apparatus for evaluating a material of an object, the apparatus comprising:

means for generating coherent parallel energy beams and coherent focusing energy beams which have different frequencies;

means for irradiating a surface of the object with the coherent parallel energy beams and the coherent focusing energy beams to excite acoustic waves focused to a small region in the object; and detecting the acoustic waves reflected by the small region or allowed to pass through the small region and then allowed to reach a front surface or a rear surface of the object with a probe beam so as to analyze characteristics of the material of the object.

According to the present invention, there is provided a method of exciting acoustic waves comprising the following steps of:

irradiating a surface of an object having a specific acoustic speed of V with coherent focusing energy beams and coherent parallel energy beams which have wavelength of λ and frequencies which are different from each other by f in such a manner that the parallel energy beams and the focusing energy beams overlap each other while locating a focal point of the focusing energy beams at depth d from the surface of the object which satisfies the following relation:

$$f \times \sqrt{\lambda^2 + 2\lambda d} > V$$

to form concentric interference fringes propagating toward an inside portion of the object; and exciting acoustic waves which are focused to a specific small region in the object in accordance with a distortion distribution generated on the surface of the object attributable to a photo-thermal effect of the interference fringes.

According to the present invention, there is provided an apparatus for exciting acoustic waves comprising:

means for irradiating a surface of an object having a specific acoustic speed of V with coherent focusing energy beams and coherent parallel energy beams which have wavelength of λ and frequencies which are different from each other by f in such a manner that the parallel energy beams and the focusing energy beams overlap each other while locating a focal point of the focusing energy beams at depth d from the surface of the object which satisfies the following relation:

$$f \times \sqrt{\lambda^2 + 2\lambda d} > V$$

to form concentric interference fringes propagating toward an inside portion of the object;

means for exciting acoustic waves which are focused to a specific small region in the object in accordance with a distortion distribution generated on the surface of the object attributable to a photo-thermal effect of the interference fringes; and means for changing a depth of the small region in the object to which the acoustic waves are focused.

According to the present invention, there is provided a method of evaluating a material of an object, the method comprising the following steps of:

exciting acoustic waves which are focused to an inside of the object by irradiating a surface of the object with coherent parallel energy beams and coherent focusing energy beams which have different frequencies such that the parallel energy beams and the focusing energy beams overlap each other;

means for changing the frequency difference f between the focusing energy beams and the parallel energy beams;

means for measuring a displacement of the object after the acoustic waves reflected by or allowed to pass through the object reach a front surface or a rear surface of the object with a probe beam; and means for evaluating a structure of the inside of the object at various depths by analyzing a frequency of a signal denoting the displacement of the object.

According to the present invention, there is provided a method of exciting acoustic waves comprising the steps of:

obtaining phase distribution of the acoustic waves propagating along a surface of the object on an assumption that the acoustic waves having a frequency of f are generated at one point in the object;

irradiating the surface of the object with coherent parallel energy beams and coherent focusing energy beams having a frequency difference of f in such a manner that the parallel energy beams and the focusing energy beams overlap each other so as to generate interference fringes propagating toward an inside portion of the object;

forming, on the surface of the object, a distortion distribution substantially the same as the obtained phase distribution of the acoustic waves on the surface of the object attributable to a photo-thermal effect of the interference fringes; and exciting acoustic waves which are focused to the point in the object.

According to the method and apparatus for exciting focusing acoustic waves according to the present invention, acoustic waves focusing to a small region in an object can be excited.

According to the method and apparatus for evaluating a material in a non-contact and non-destructive manner have the structure such that the position to which acoustic waves are focused is three-dimensionally scanned so that a defect, the structure, and film thickness et al. of a small region in an object are precisely evaluated with high resolution.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 shows parallel energy beams for use in an operation according to the present invention for exciting acoustic waves;

FIG. 2 shows focusing energy beams for use in exciting acoustic waves;

FIG. 3 shows parallel energy beams and focusing energy beams with which the surface of an object is irradiated when the acoustic waves are excited;

FIG. 5 shows the principle of exciting the focus acoustic waves;

FIG. 6 shows results of a simulation of excitation of the acoustic waves;

FIG. 19 is a diagram showing the structure of an interferometer adapted to the Fabry-Pérot method serving as another example of the analyzer according to the embodiment of the present invention;

FIG. 20 shows another embodiment of the non-contact and non-destructive evaluating apparatus according to the present invention;

FIG. 21 shows another example of interference fringes for use in exciting acoustic waves;

DETAILED DESCRIPTION OF THE PREFERRED EMBODIMENTS

A preferred embodiment of a method and apparatus for exciting bulk acoustic waves according to the present invention will now be described with reference to the accompanying drawings. Initially, excitation of focusing bulk acoustic waves will now be described.

Figure 4:
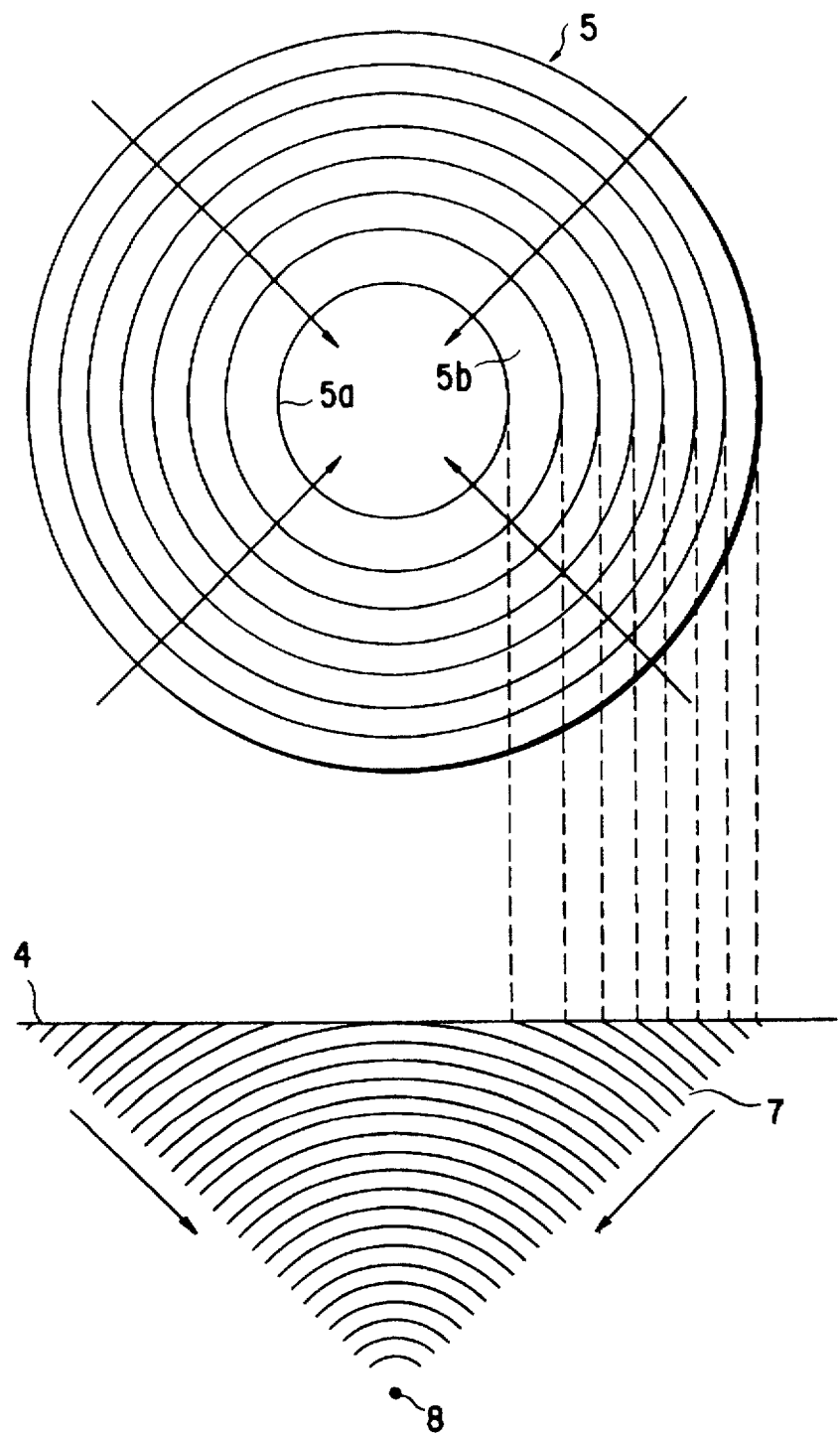
FIG. 4 shows an example of interference fringes for use in exciting acoustic waves.

Parallel energy beams (for example, laser beams) 1 having an angular frequency ω as shown in FIG. 1 and focusing energy beams 2 having an angular frequency ω' as shown in FIG. 2 are emitted to irradiate the surface 4 of the object 3 in a direction perpendicular to the same in such a manner that the parallel energy beams 1 and the focusing energy beams 2 intersect, as shown in FIG. 3. Each line indicating the parallel energy beams 1 and the focusing energy beams 2 schematically shows wave surfaces having the same phase. The phases of the parallel energy beams and the focusing energy beams interfere with each other on the surface 4 of the object 3 as shown in FIG. 3 so that interference fringes 5 in the form of concentric circles as shown in FIG. 4 are generated.

The interference fringes 5 propagate from the outer periphery to the internal center in such a manner that the intervals between the concentric circles are elongated in the direction toward the center. Lines 5a of the concentric circles shown in FIG. 4 show light portions and portions 5b between the lines 5a show dark portions. The light portions 5a and the dark portions 5b of the interference fringes supply heat energy to the object 3 by different amounts. As a result, the amount of expansion becomes different so that dynamic distortion distribution is generated on the surface 4 of the object 3 along the concentric circles of the interference fringes. Thus, bulk acoustic waves 7 vibrating at an angular frequency of |ω'-ω| are excited from the foregoing position toward the inside portion of the object 3. The bulk acoustic waves 7 are focused toward a focus point 8 which is a small region in the object 3.

FIG. 5 schematically shows the foregoing operation. Referring to FIG. 5, the surface 4 of the object 3 is made such that z=0 (the direction of the depth is direction z) and the distance from the surface 4 to a focus point 9 of the focusing energy beams 2 is made to be d. As described above, the bulk acoustic waves 7 are excited from the surface 4 toward the inside portion of the object 3 so as to be focused toward the focus point 8. The point on the surface 4, at which z=0, and just above the focus point 8 is made such that x=0 (the horizontal direction of the figure is direction x). Bulk acoustic waves 7 having a radiation angle of φ are applied toward the focus point 8 in the object 3 from the respective points on the surface 4. Assuming that the angular frequencies of the parallel energy beams 1 and the focusing energy beams 2 respectively are ω and ω' and the wavelength of the focusing energy beams 2 is λ, distance b among the interference fringes 5 is expressed by Equation (1):

$$b = \lambda \times \frac{\sqrt{d^2 + x^2}}{x} \qquad (1)$$

Since the interference fringes 5 have a frequency of f=|ω'-ω|/2π, scanning speed (propagation speed) v of the bulk acoustic waves 7 from the outside of the interference fringes 5 on the surface 4 to the center of the object 3 is expressed by Equation (2):

$$v = f \times \frac{\lambda \times \sqrt{d^2 + x^2}}{x} \qquad (2)$$

Assuming that the specific acoustic speed of the object 3 is V, satisfaction of a condition v>V between the scanning speed v of the interference fringes 5 and the specific acoustic speed V expressed by Equation (2) enables the bulk acoustic waves 7 propagating to the inside portion of the object 3 to be generated. The radiation angle φ of the bulk acoustic waves 7 at each point on the surface 4 can be obtained from Equation 3 below in accordance with Snell's law:

$$\phi = \sin^{-1}\left( \frac{V/f}{\lambda \times \frac{\sqrt{d^2 + x^2}}{x}} \right) \qquad (3)$$

FIG. 6 shows the bulk acoustic waves 7 simulated by the three equations above. The simulation is performed under conditions that the energy beam was laser beams having a wavelength λ=532 nm and the frequency of the interference fringes is modulated by f=|ω'-ω|/2π=100 MHz. Note that the relationship ω'>ω must be satisfied. If a contrary relationship is realized, acoustic waves diffusing radially are unintentionally excited. The specific acoustic speed V in the object 3 was made to be 5000 m/s. The distance d from the surface of the object 3 to the focus point 9 for the focused laser beams was made to be 10 cm. Note that unit in the FIG. 6 is meter and only one side of the result of the simulation is illustrated. As can be understood from the result shown in FIG. 6, the interference fringes 5 having a beam radius of about 0.6 |mm| result in the bulk acoustic waves being focused to a focus point which is about 1 mm depth while extending to have a width of about 150 |μm|.

Although the foregoing simulation performed on the assumption that the focusing laser beams are spherical waves having a completely spherical phase surface results in incomplete focusing to one point, use of aspheric lens as the lens for converting the parallel beams emitted by the laser source into focusing beams enables bulk acoustic waves which are completely focused to one small region to be excited.

Note that the necessity of using completely parallel laser beams as the parallel laser beams can be eliminated. Any beams propagating substantially in parallel formed by a lens having a somewhat long focal distance is able to excite the focusing bulk acoustic waves.

Figure 7:
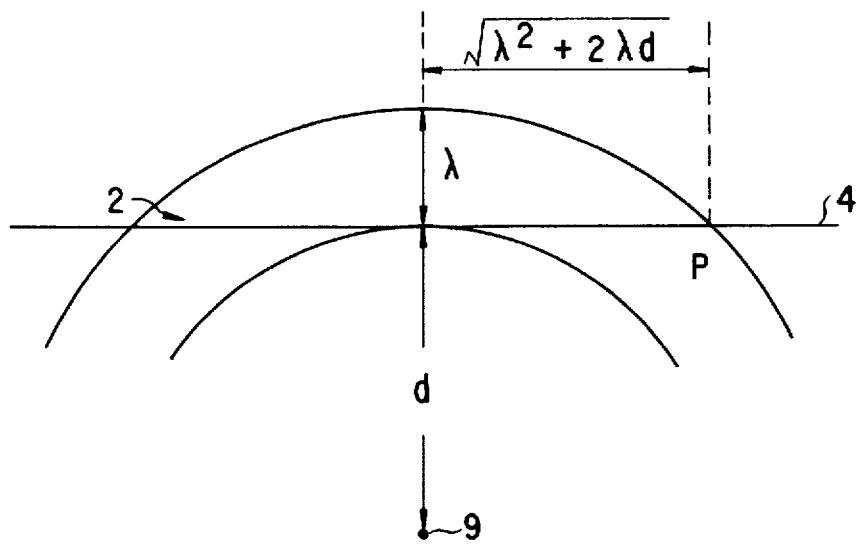
FIG. 7 shows focusing characteristic of bulk acoustic waves.

Even if the surface of the object is perpendicularly irradiated with the overlapping focusing laser beams and the parallel laser beams, the focusing bulk acoustic waves are not always generated in the inside portion of the object. The focus point 9 of the focusing energy beams 2 must be positioned at the depth of d from the surface 4 of the object 3 as shown in FIG. 7, the depth d being larger than a predetermined value.

In the case where waves are radiated from a finite and parallel oscillation surface and then the waves are focused to a certain position (the focal point), the focusing property can approximately be evaluated in accordance with the number of periods of the wave phases included in the oscillation surface. An assumption is made here that the focus point 9 of the focusing energy beams 2 having the wavelength of $\lambda$ is positioned at a position of depth d from the surface of the object 3 and the surface of the object 3 is perpendicularly irradiated with the parallel laser beams. Assuming that the difference between the frequency of the focusing laser beams and that of the parallel laser beams is f and phase change of the wave of distortion in the oscillating surface from which the excited acoustic waves are able to obtain sufficient focusing property is one period, the phase speed of a mean wave surface at a distance from a position of the surface just above the focus point 8 to position P apart the surface by one period is expressed by $f \times \sqrt{\lambda^2 + 2\lambda d}$, as shown in FIG. 7. If the phase speed is slower than the specific acoustic speed V of the object, acoustic waves cannot be introduced into the object and focused. Since acoustic waves which can be generated in a usual isotropic solid material include longitudinal waves and transversal waves which respectively have specific acoustic speeds, V in the condition $f \times \sqrt{\lambda^2 + 2\lambda d} > V$ depends upon the type of the acoustic wave intended to be focused.

As described above, according to the present invention, bulk acoustic waves focusing to a small region in an object can be excited. By three-dimensionally moving the object, each region in the object can be scanned by the bulk acoustic waves so that the position of a defect in the object is detected.

The focus point for the bulk acoustic waves can be changed by changing the depth d of the focus point of the focusing laser beams or the frequency difference f between the focusing laser beams and the parallel laser beams.

Change in depth D at which the acoustic waves are focused when the depth d of the focal point of the focusing laser beams has been changed is shown in Table 1. Assumptions are made here that the acoustic speed V of the object is 3000 m/s and frequency difference f is 100 MHz.

TABLE 1

| d (focus length of laser beam) |mm| | 50 | 70 | 100 | 150 |
|---|---|---|---|---|
| D (focus length of acoustic wave) |mm| | 0.8 | 1.2 | 1.7 | 2.5 |

Figure 8:
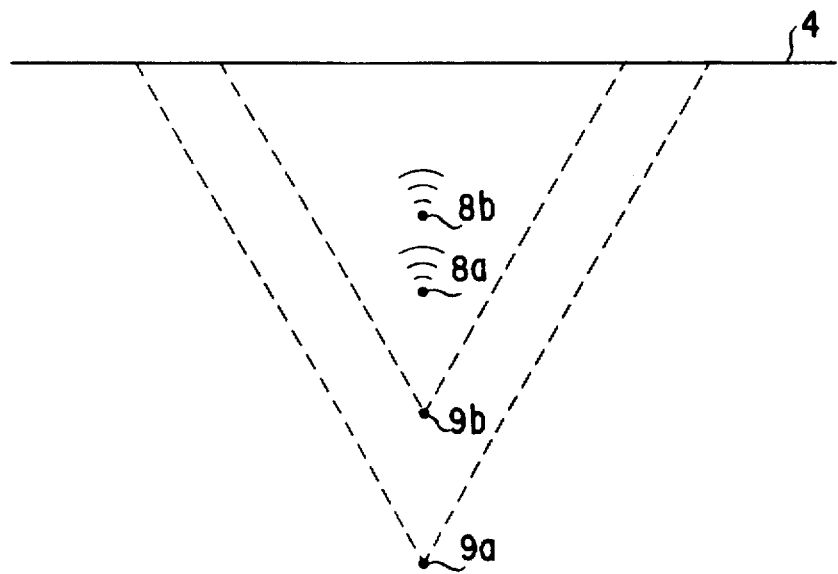
FIG. 8 shows the relationship between focus points of focusing energy beams and focus points of bulk acoustic waves.

As shown in Table 1, as the depth d of the focal point 9 of the focusing laser beams is increased, the focus depth D of the acoustic waves which are excited in the object is increased. FIG. 8 illustrates the foregoing fact. That is, in a case where the focal point of the focusing laser beams is deep as indicated by 9a, the focus point of the excited acoustic wave is made as indicated by 8a. In a case where the focus position of the focusing laser beams is at point 9b which is shallower than point 9a, the focus position of the acoustic wave is made to be point 8b which is shallower than point 8a. As described above, change of the focus depth of the focusing laser beams enables the focus depth D of the acoustic wave to arbitrarily be changed.

Figure 9:
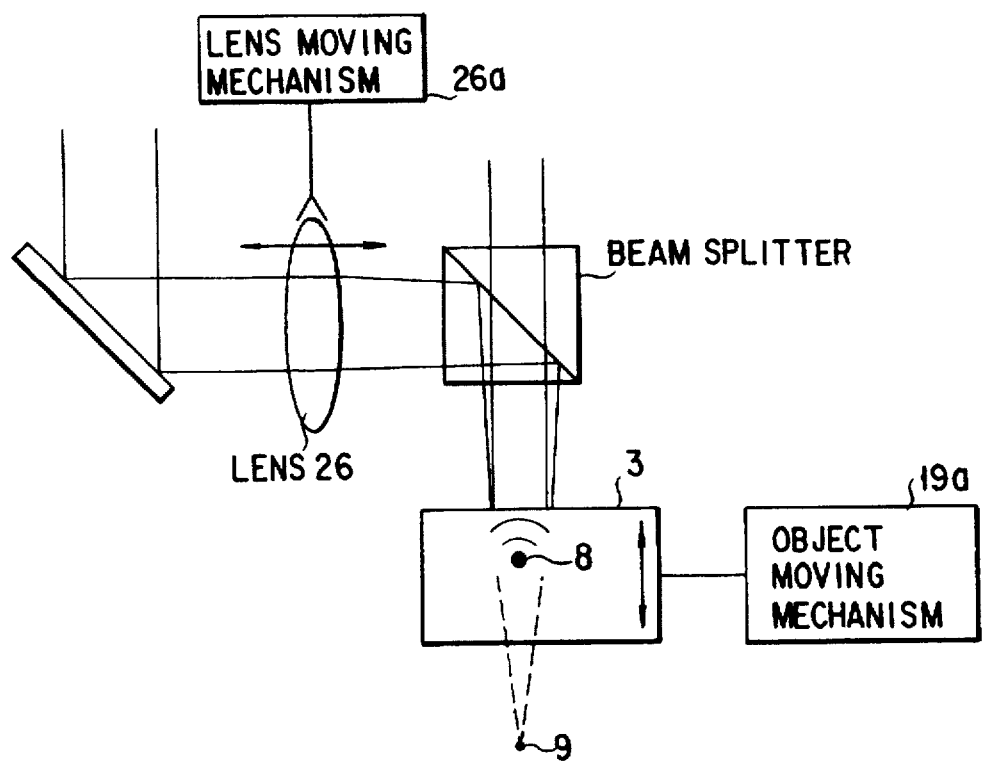
FIG. 9 is a block diagram showing a mechanism for shifting the focus point of focusing energy beams.

As a means for changing the focus depth d of the focusing laser beams, a converging lens 26 serving as a means for forming focusing laser beams or the object 3 may mechanically be moved, as shown in FIG. 9. A lens moving mechanism 26a for horizontally moving the converging lens 26 is connected to the converging lens 26. As an alternative to this, an object moving mechanism 19a for vertically moving the object 3 is connected to the object 3. In this case, the distance for which the converging lens and the object are moved is not the same as the distance of movement for the focusing laser beams. They must be moved tens of times the distance of movement of the focus depth. If a focal-distance changing mechanism generally called a "zoom lens" is used as the lens moving mechanism 26a, the focus position can considerably be changed by moving the lens for a very short distance so that a multiplicity of points can quickly be measured in the direction of the depth of the object.

A method of changing the focus depth of the acoustic wave by changing the frequency difference f will now be described. Table 2 shows change in the focus depth D of the acoustic wave excited when the frequency difference f is changed when the acoustic speed of the object is 3000 m/s and the focus depth of the focusing laser beams is 10 cm.

TABLE 2

| f (frequency difference) [MHz] | 70 | 100 | 130 | 160 |
|---|---|---|---|---|
| D (focus length of acoustic wave) [mm] | 1.2 | 1.7 | 2.5 | 2.7 |

Figure 10:
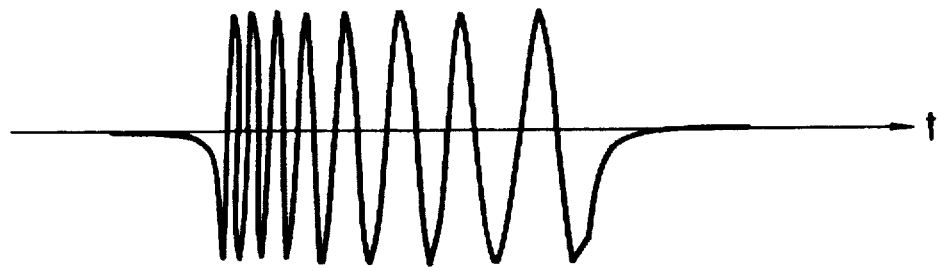
FIG. 10 is a graph showing the waveform of a chirp signal for changing the frequency difference between focusing energy beams and parallel energy beams in order to shift the focus point of the focusing energy beams.

Change of the frequency f can be performed by changing a control signal which is supplied to an acoustic optical device which is introduced into an intermediate position for realizing the frequency difference f between the parallel laser beams and the focusing laser beams into a chirp waveform as shown in FIG. 10. By using the foregoing chirp signal, the difference between the frequency of the parallel laser beams and that of the focusing laser beams can successively be changed during one operation of irradiation with the laser beams. Thus, acoustic waves which are focused to different depths can be excited by one irradiation with the laser beams.

Figure 11A:
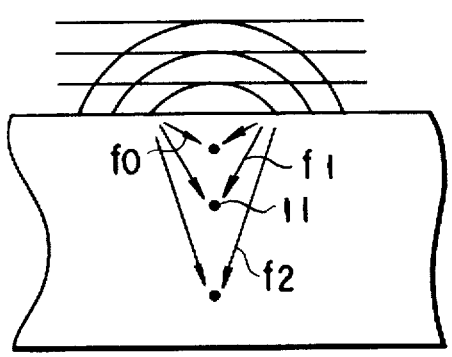
FIGS. 11A and 11B are diagrams showing the principle of detecting the depth of a defect in an object.
Figure 11B:
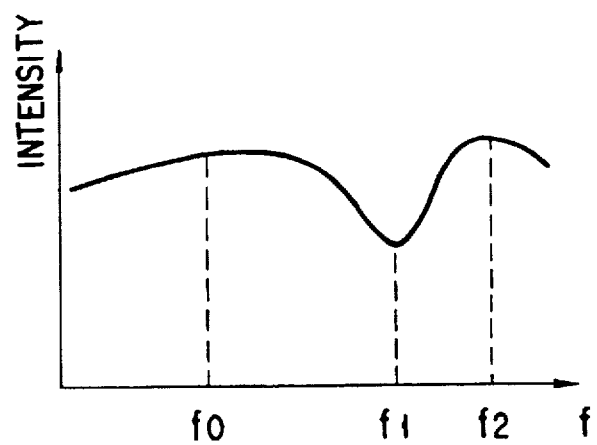

Then, displacement observed on the surface of the object attributable to an echo of the excited acoustic waves is observed by, for example, an optical means; and then the frequency of a signal denoting the observed surface displacement is analyzed. Thus, a result can be obtained in which the acoustic wave characteristics of the object are included. That is, FIG. 11A shows a state where the focus depth is changed attributable to change in the frequency difference f in which a defect 11 is generated at the position of the focus depth when the frequency difference is f1. FIG. 11B is a graph having an axis of abscissa standing for the frequency difference f and an axis of ordinate standing for the acoustic wave characteristics of the object so as to show the intensity of the signal denoting the surface displacement. Since displacement generated on the surface of the object by the acoustic waves from a portion having the defect is different from the displacement generated on the surface of the object by the acoustic waves from a portion having no defect, observation of the displacement by an optical means enables the defect generated in the object to be detected by frequency analysis which is performed as shown in FIG. 11B.

Figure 12:
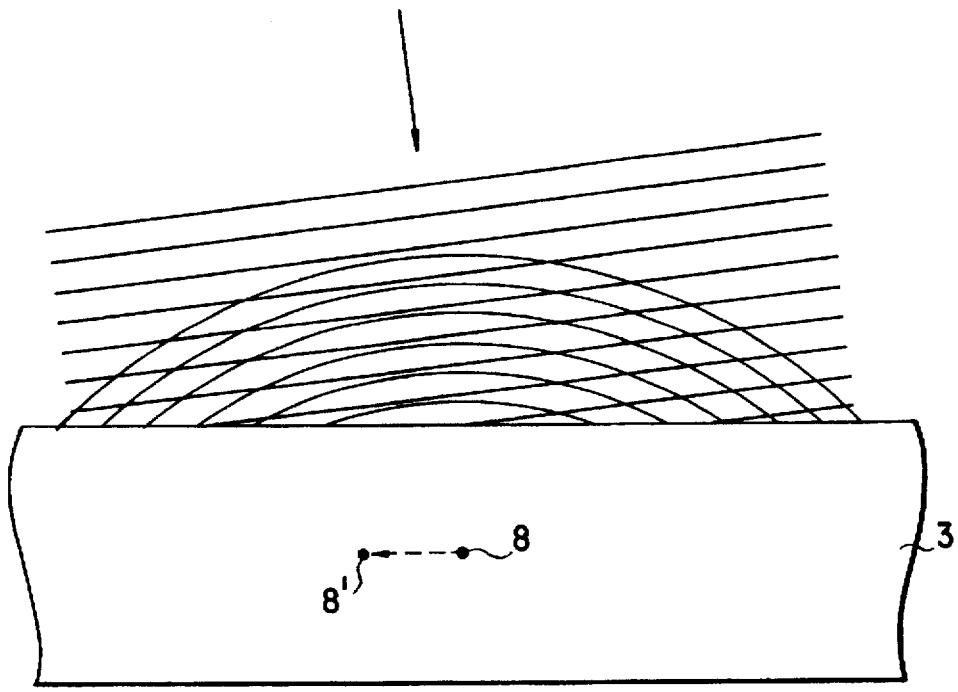
FIG. 12 shows an operation for, in parallel, translating the focus point of bulk acoustic waves by changing the incident angle of parallel energy beams.

The movement of the focus point of the bulk acoustic waves into a direction of the depth of the object has been described. Movement into a direction along the surface of an object will now be described. As shown in FIG. 12, when the parallel laser beams are made incident on the surface of the object while making a certain inclined angular degree, the focus position of the bulk acoustic waves in the object can be moved or shifted in parallel from point 8 to point 8'.

Figure 13:
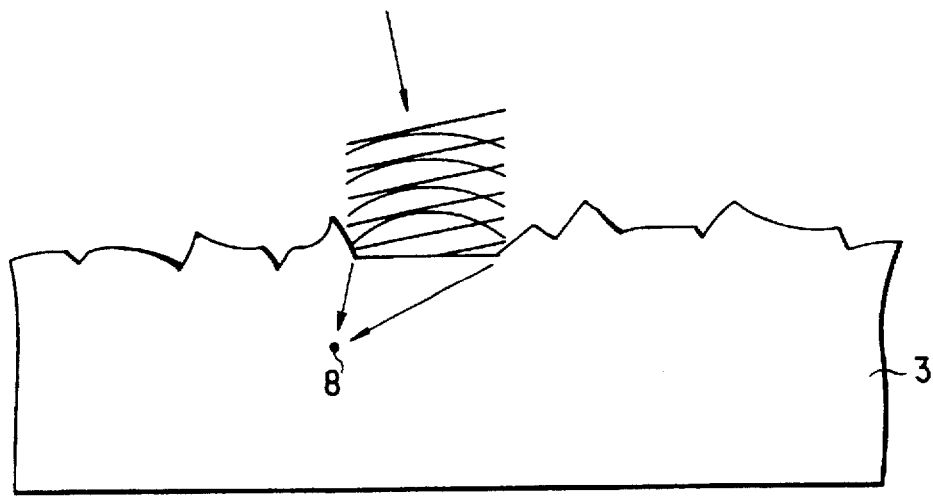
FIG. 13 is a diagram showing an application of the structure shown in FIG. 12.

As a result, the focus position (or the observation point) can arbitrarily be moved in the directions x and y without moving the object or the laser beam irradiation means only by changing the incident angle of the parallel laser beams. The foregoing method is convenient in a case shown in FIG. 13 in which the surface of an object is roughened and a region on the surface of the object, in which the interference fringes can be formed, is limited.

Figure 14:
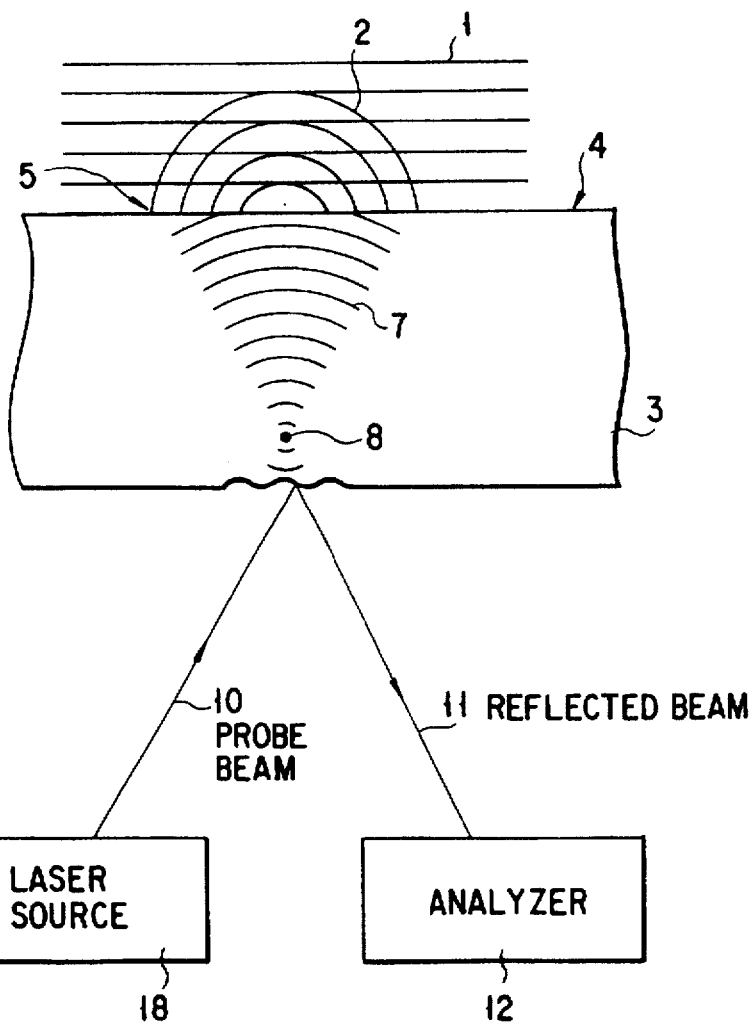
FIG. 14 is a diagram showing the principle of evaluation of a material in a non-contact and non-destructive manner according to the present invention.

Then, evaluation of the material of an object in a non-contact and non-destructive manner by using the focusing bulk acoustic waves excited as described above will now be described. FIG. 14 is a diagram showing the principle of the foregoing method. The parallel laser beams 1 and focusing laser beams 2 are perpendicularly made incident on the surface of the object 3 so that the interference fringes 5 are formed on the surface. When the interference fringes 5 are moved from outside to the inside, the bulk acoustic waves 7 focusing to the certain point 8 in the object 3 are excited. The bulk acoustic waves 7, allowed to pass through the focus point 8, reach the rear surface of the object 3, thus causing minor distortion to be generated on the rear surface attributable to the bulk acoustic waves 7. When the rear surface is irradiated with a probe beam 10 from a probe laser source 18, a reflected beam 11 corresponding to the minor distortion can be obtained. The reflected beam 11 is detected and analyzed by any one of a variety of detector and analyzer 12 to be described later. Therefore, the characteristics of the material of the object 3 are analyzed or detection of abnormal fact, such as a defect, in the material of the object 3 is performed in a non-contact and non-destructive manner. Note that the probe beam 10 may be applied to the front surface of the object 3 in place of the rear surface so as to detect bulk acoustic waves reflected by the focus point.

Figure 15:
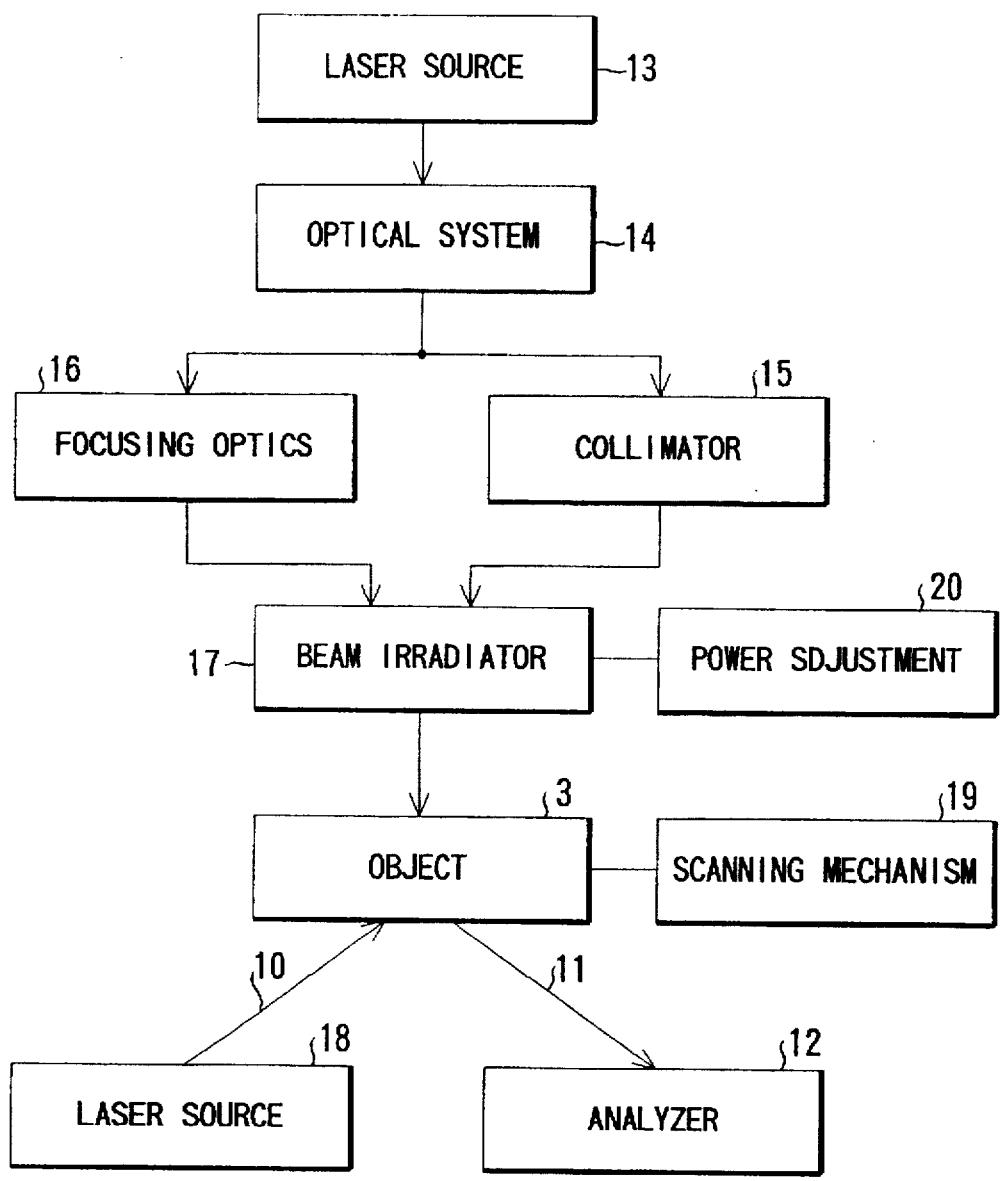
FIG. 15 is a block diagram showing the schematic structure of a non-contact and non-destructive evaluating apparatus according to the present invention for evaluating a material.

A material evaluation mechanism structured on the basis of the foregoing principle will now be described. FIG. 15 is a block diagram showing the overall structure of the mechanism according to this embodiment. Laser beams emitted by a laser source are, through an optical system 14, converted into parallel laser beams 1 having an angular frequency ω and focusing laser beams 2 having angular frequency ω' by a collimator 15 and a focusing optics 16. The parallel laser beams 1 and the focusing laser beams 2 are used to irradiate the surface 4 of the object 3 through a beam irradiator 17. As shown in FIG. 4, the bulk acoustic waves focusing to one point are generated in the object 3.

The probe beam 10 emitted from the laser source 18 is applied to the rear surface of the object 3. A reflected beam 11 from the object 3 is, as shown in FIG. 14, made incident on the analyzer 12 for detecting and analyzing the characteristics of the material so that predetermined detection and analysis processes are performed. A scanning mechanism 19 for moving the object 3 in the directions x and y is connected to the object 3. An acoustic optical device (not shown) which is operated in response to a chirp signal so as to change the frequency difference f between the focusing laser beams and the parallel laser beams as shown in FIG. 10 is provided for either of the collimator 15 or the focusing optics 16. By arbitrarily moving the object 3 by the scanning mechanism 19 and by changing the frequency difference f between the focusing laser beams and the parallel laser beams, all positions in the object 3 can be detected.

In order to make the parallel laser beams 1 and focusing laser beams 2 to completely interfere with each other, a power adjuster 20 for making the energy density of the two types of the beams to be the same is provided for the beam irradiator 17. The power adjuster 20 may be connected to any point following the optical system 14.

According to the foregoing structure, bulk acoustic waves focusing to a small region in the object 3 can be excited. Moreover, material evaluation can be performed such that the excited bulk acoustic waves are used to detect and analyze the characteristics of the material in a non-contact and non-destructive manner.

Figure 16:
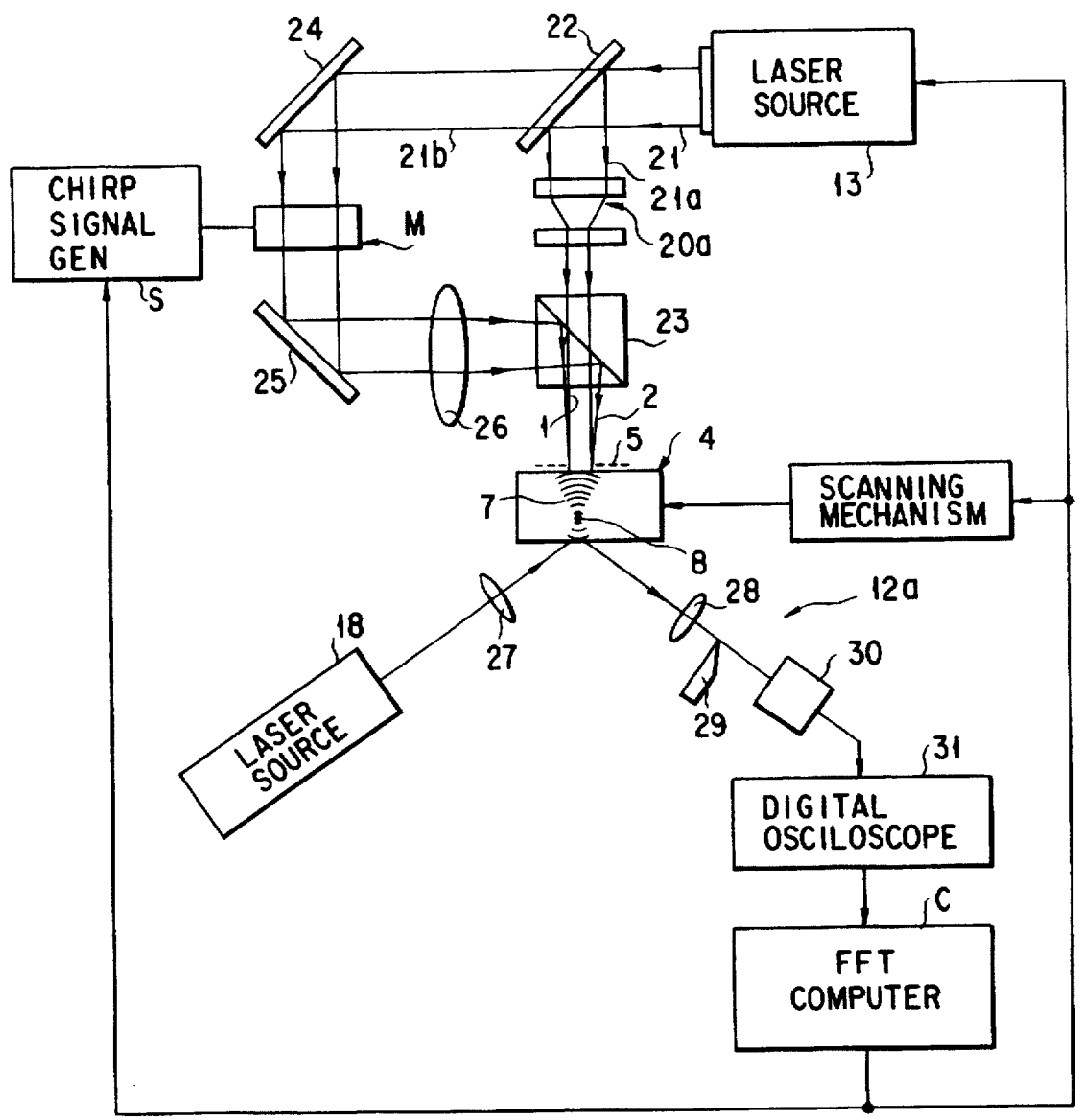
FIG. 16 is a block diagram showing an embodiment of the non-contact and non-destructive evaluating apparatus according to the present invention.

FIG. 16 shows an embodiment of a material evaluation mechanism according to the present invention for evaluating the material in a non-contact and non-destructive manner. A laser beam 21 emitted from the laser source 13 is divided into two laser beam 21a and 21b by a half mirror 22. The laser beam 21a is allowed to pass through a beam-diameter adjuster 20a, which is an example of the power adjuster 20, and then allowed to pass through the beam splitter 23 serving as the collimator 15 and the beam irradiator 17, so as to be applied to the surface 4 of the object 3 as the parallel laser beams 1. The other laser beam 21b is, through a mirror 24, made incident on an acoustic optical device M. A chirp signal generator S is connected to the acoustic optical device M so that the frequency of the laser beam is modulated. The laser beam allowed to pass through the acoustic optical device M is allowed to pass through a mirror 25, a converging lens 26, and a beam splitter 23 serving as the focusing optics 16 and the beam irradiator 17, so as to be applied to the surface 4 of the object 3 as the focusing laser beams 2. As a result, the bulk acoustic waves 7 focusing to the focus point 8 are generated in the object 3.

The object 3 is provided with the scanning mechanism 19 for moving the object 3 in the directions of x and y. A control signal having the frequency which is successively changed as shown in FIG. 10 is supplied from the chirp signal generator S to the acoustic optical device M. Therefore, the bulk acoustic waves can three-dimensionally be scanned in the object. As described above, the chirp signal generator and the acoustic optical device may be omitted from the structure and the converging lens 26 and the object 3 may mechanically be moved to change the depth of the focus point of the focusing laser beams 2 so as to change the depth of the bulk acoustic waves.

The probe beam 10 emitted from the laser source 18 is, through the converging lens 27, applied to the rear surface of the object 3. Reflected beam 11 from the rear surface is detected and analyzed by a knife edge analyzer 12a adapted to the principle of the knife edge method and serving as an example of the analyzer 12. The knife edge analyzer 12a comprises a converging lens 28, a knife edge 29, a photodiode 30, and a digital oscilloscope 31. Reflected beam 11 from the object 3 is processed such that either of the upper or lower portion of the spot of the reflected beam 11 is cut by the knife edge 29. As a result, change in the reflection angle of the reflected beam 11 occurring attributable to the unevenness of the surface of the object and corresponding to the bulk acoustic waves can be detected. Thus, the intensity of the bulk acoustic waves 7 can accurately be performed. Note that the digital oscilloscope 31 and the scanning mechanism 19 are connected to an FFT (Fast Fourier Transform) computer C. Note that the computer C performs analysis and calculations of a defects in the material and the characteristics of the material.

A result of an actual operation of the embodiment shown in FIG. 16 will now be described. The radius of the beam on the surface 4 of the object 3 was about 0.5 [mm] and the object 3 was a steel plate having a thickness of 1 [mm]. In this case, the specific acoustic speed (the longitudinal waves) of the steel plate was about 4700 m/second. Laser beams polarized completely and having a wavelength of 532 [nm] was oscillated by a second harmonic of a Q switch Nd-YAG pulse laser, and the pulse width of the laser beam was made to be 50 nsec. The oscillated laser beam was divided to pass through two passages by the beam splitter. The frequency of the laser beam 21b of the two laser beams 21a and 21b was modulated by the acoustic optical device M by 100 MHz. To make the two laser beams 21a and 21b to completely interfere with each other, the beam-diameter adjuster 20a or the like was used to adjust the energy density of the parallel laser beams 21a and the focused laser beams 21b on the surface of the object to be the same.

Figure 17:
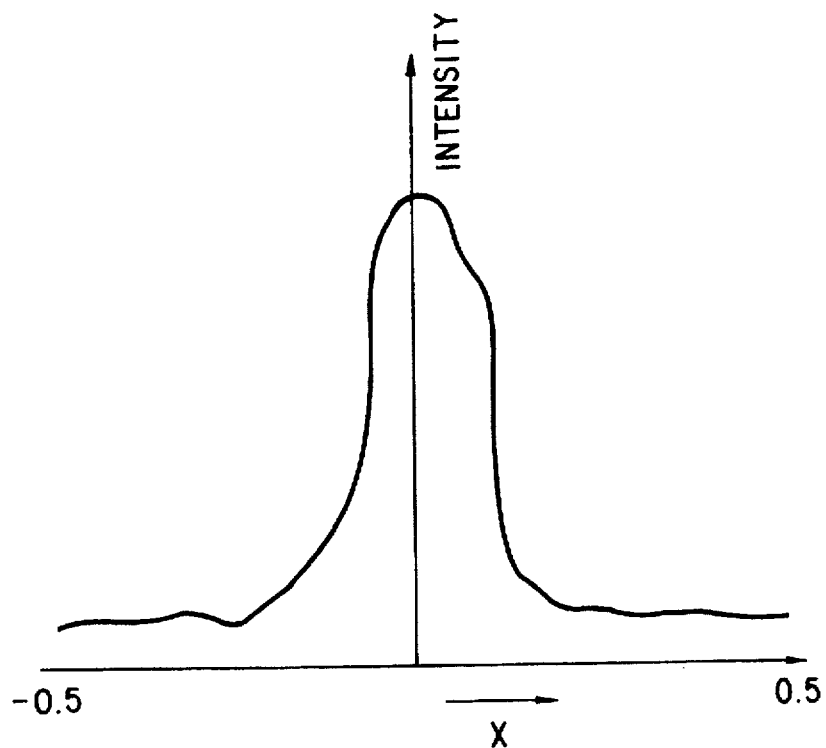
FIG. 17 is a graph showing results of the operation of the embodiment according to the present invention.

The intensity of the bulk acoustic waves 7 detected by the analyzer 12 is shown in FIG. 17. FIG. 17 has an axis of abscissa standing for x coordinates and an axis of ordinate standing for the intensities (the relative values) of the bulk acoustic waves when the focus point of the focusing laser beam is scanned in the x direction (surface direction) of the object 3. As shown in FIG. 17, a fact that the bulk acoustic waves was reached the rear surface of the object immediately below the focus point 8 was detected by the knife edge method.

Although the embodiment shown in FIG. 16 has been described about the knife edge analyzer 12a which serves as the analyzer 12, a heterodyne interferometer method or a Fabry-Pérot interferometer method may be employed.

Figure 18:
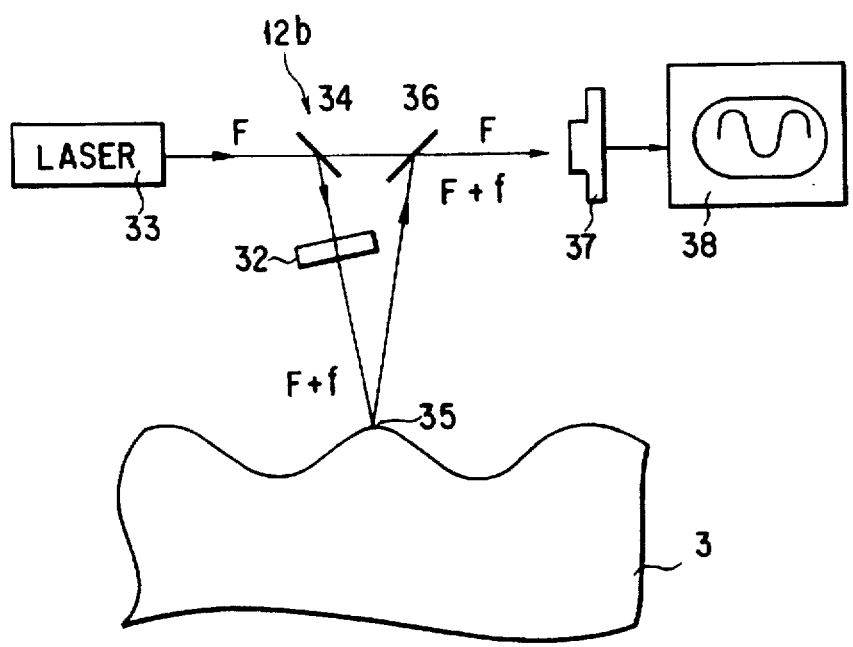
FIG. 18 is a diagram showing the structure of a heterodyne interferometer method serving as another example of the analyzer according to the embodiment of the present invention.

FIG. 18 shows the principle structure of a heterodyne-method interferometer 12b. A laser beam having frequency F is emitted from a laser source 33, and then the laser beam is branched into two sections by a half mirror 34. The frequency of either of the two reflected beams is, by an acoustic optical device 32, modulated into a frequency of F+f and the modulated beam is irradiated on the surface of the object 3. As described above, a small displacement 35 is formed on the surface of the object 3 attributable to the bulk acoustic waves so that the laser beam having the frequency of F+f is reflected by the portion of the small displacement 35.

The reflected beam and the beam allowed to pass through the half mirror 34 is made incident upon a half mirror 36, and then mixed by a half mirror 36. However, the laser beams respectively having the frequency of F and that of F+f interfere with each other, thus resulting in beat being generated. A beam reflected by the half mirror 36 is converted into an electric signal by a photodiode 37, and then observed by an oscilloscope 38 so that the "change in the phase of the beat" is detected.

Assuming that the displacement on the surface of the object corresponds to ¼ of the wavelength of the laser beam, also the phase of the "beat" generated attributable to the interference between the reflected laser beam and the laser beam directly propagated from the half mirror 34 to the half mirror 36 is shifted by a distance corresponding to half of the wavelength of the "beat". Since the "beat" signal is a signal having a low frequency similar to that the modulation frequency, change in the phase of the "beat" can easily be observed by an oscilloscope 38.

As described above, the heterodyne method enables the change in the phase of the beat to be measured to observe slight displacement similar to the wavelength of light on the surface.

FIG. 19 shows an interferometer 12c adapted to the Fabry-Pérot method in which an interferometer comprising semitransparent mirrors 39 and 40 for extracting and transmitting a beam having a specific frequency (a wavelength) is used. A beam emitted from a laser source 41 and having a frequency of F is reflected by a displaced portion 42 (which is vibrated with frequency f) on the surface of the object 3. The frequency F of the reflected beam is, attributable to the Doppler effect, changed to frequency F'. The interferometer comprises the mirrors 39 and 40 in such a manner that only a beam except a beam having the frequency of F, for example, F' is extracted. As a result, the beam having the frequency of F' is made incident upon a photodiode 43 so as to be converted into an electric signal. The electric signal is observed by an oscilloscope 44 so that displacement generated in the object 3 is observe.

FIG. 20 shows another embodiment of a material evaluation mechanism which is a modification of FIG. 16. In FIG. 16, transmission acoustic waves passing the defect are detected by the probe laser beam. In FIG. 20, acoustic waves reflected by a defect 100 are detected by the probe laser beam. Other portions are the same as those of FIG. 16.

As described above, according to this embodiment, the following effects can be obtained.

(1) Coherent parallel laser beams and focusing laser beams having different frequencies are irradiated onto the surface of an object to form interference fringes propagating from outside to the inside portion. Under condition that the propagation speed of the interference fringes is higher than the specific acoustic speed of the object, bulk acoustic waves focusing to a predetermined point in the object can easily be excited.

(2) By applying a probe beam and by scanning the object, a defect, the material and characteristics of an arbitrary small region in an object can accurately be detected by a non-contact and non-destructive manner. Therefore, the material can be evaluated more accurately and efficiently with high spatial resolution as compared with the conventional technology.

(3) By shifting the focal position of the focusing laser beams or by changing the frequency difference between the parallel laser beams and the focusing laser beams, the depth in the small region of the object to which the bulk acoustic waves are focused can be adjusted successively or in a stepped manner. Therefore, a flaw in the inside portion can quickly be detected.

The present invention is not limited to the abovementioned embodiment and a variety of modifications may be permitted. Although the structure has been described in which the interference fringes 5 having the intervals which are successively changed (the intervals are increased in the direction toward the inside portion) are formed, the foregoing structure is realized because the spherical wave having a spherical phase surface is employed as the focusing laser beams 2. When a focusing laser beams having a required aspherical phase is employed, concentric interference fringes 5' having the same intervals as shown in FIG. 21 are formed. Bulk acoustic waves 7' generated in accordance with the distortion distribution generated on the surface 4 of the object 3 attributable to the interference fringes 5' are focused to focus point 8a in the form of a vertical straight line, as shown in FIG. 21. As a result, the characteristics of the material in the direction of the depth can be inspected by one laser irradiation. Thus, the labor for evaluating the material can be saved. Note that the resolution in the direction of the depth of the material can be obtained depending upon the difference in the detection time of a signal of the reflected acoustic waves. The interval h of the interference fringes 5' must have the following relation:

$V < h \cdot f$

As described above, the shape of the focusing laser beams is changed so that interference fringes having an arbitrary shape are formed and the focus position of the bulk acoustic waves is arbitrarily set. If focusing laser beams having a cylindrical phase surface are employed, bulk acoustic waves can be focused on a horizontal straight line.

In the above description, it is assumed that the object 3 is an isotropic object. The present invention can be applied to an anisotropic object. In the case of the anisotropic material, the specific acoustic speed of the material is, however, different owning to the direction or angle of incidence of the laser beam. Therefore, the pattern of the interference fringes focused in the object by the excited acoustic wave is not formed into the concentric circles. By distorting the focusing laser beams or the parallel laser beams, the shape of the interference fringes can be controlled to excite required bulk acoustic waves.

Figure 22:
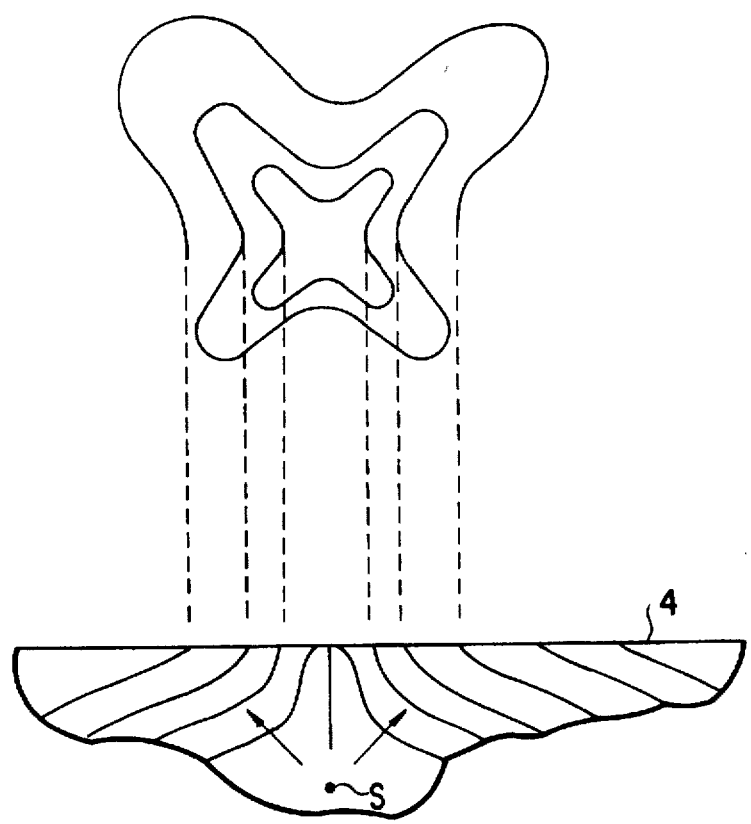
FIG. 22 is a diagram showing an example of phase distribution generated on the surface of an object by acoustic waves in the case where the object is an anisotropic material.
Figure 23:
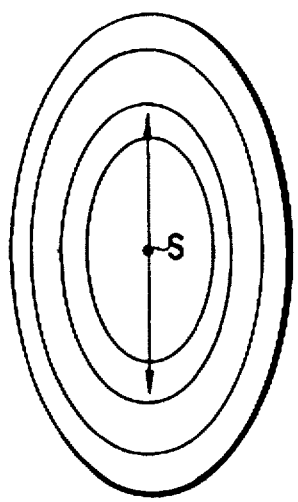
FIG. 23 is a diagram showing another example of phase distribution in the anisotropic material.

FIG. 22 shows a distorted phase distribution formed on the surface of an object by acoustic waves radiated from a point S in an anisotropic object. It is assumed that acoustic waves having a frequency f is excited at a point S in the anisotropic object 4 and acoustic waves having a phase distribution as shown in FIG. 22 transmitted to the surface of the object 4. Coherent parallel laser beams and focusing laser beams having different frequencies for generating a distortion distribution which is the same or approximate a phase distribution of the acoustic waves are applied to the surface of an object so that interference fringes propagating from outside toward the inside portion is formed. At a surface of the object, the photo-thermal operation of the interference fringes enables distortion having the same phase distribution as the phase distribution of the acoustic wave shown in FIG. 22 to be formed. As a result, bulk acoustic waves focusing toward the point S in the object can be excited. FIG. 23 shows another example of the anisotropic phase distribution formed on the surface of an anisotropic object attributable to acoustic waves generated in the anisotropic object.

As described above, according to the present invention, the following effects can be obtained.

(1) Coherent parallel laser beams and focusing laser beams having different frequencies are applied to the surface of an object to form interference fringes propagating from outside to the inside portion. Under condition that the propagation speed of the interference fringes is higher than the specific acoustic speed of the object, bulk acoustic waves focusing to a predetermined point in the object can easily be excited. The bulk acoustic waves can be employed in an operation in which the operation is preferably performed while vibrating the workpiece, for example, a process for manufacturing a semiconductor as well as inspection and evaluation of an object.

(2) The bulk acoustic waves can easily be focused to a specific position in an object attributable to the shape of the focusing laser beams. According to the circumstances, the bulk acoustic waves can simultaneously be focused to a multiplicity of focus positions along a straight line.

(3) By applying a probe beam and by scanning the object, a defect, the material and characteristics of an arbitrary small region in an object can accurately be detected by a non-contact and non-destructive manner. Therefore, the material can be evaluated more accurately and efficiently with high spatial resolution as compared with the conventional technique.

(4) By shifting the focal position of the focusing laser beams or by changing the frequency difference between the parallel laser beams and the focusing laser beams, the depth in the small region of the object to which the bulk acoustic waves are focused can be adjusted successively or in a stepped manner. Therefore, a flaw in the inside portion can quickly be detected.

(5) Even if an object has anisotropic characteristic, the structure, in which an assumption is made that the acoustic waves are generated in one point in the object and calculations are performed in consideration of the anisotropic characteristic to estimate the phase distribution of the acoustic waves on the surface of the object so as to generate interference fringes corresponding to the phase distribution, enables bulk acoustic waves focusing to the foregoing point to be excited. As a result, even an anisotropic object can similarly be inspected.

What is claimed is:

1. A method of evaluating a material of an object, the method comprising the following steps:

exciting acoustic waves which are focused to an inside of the object by irradiating a surface of an object with coherent parallel energy beams and coherent focusing energy beams, said coherent parallel energy beams and said coherent focusing energy beams having different frequencies such that the parallel energy beams and the focusing energy beams overlap each other;

means for changing the frequency difference f between the focusing energy beams and the parallel energy beams;

means for measuring a displacement of the object after the acoustic waves reflected by or allowed to pass through the object reach a front surface or a rear surface of the object with a probe beam; and means for evaluating a structure of the inside of the object at various depths by analyzing a frequency of a signal denoting the displacement of the object.

2. A method of evaluating a material of an object, the method comprising the following steps of:

irradiating a surface of an object having a predetermined specific acoustic speed with coherent parallel energy beams and coherent focusing energy beams, said coherent parallel energy beams and said coherent focusing energy beams having different frequencies such that the parallel energy beams and the focusing energy beams overlap each other to generate interference fringes in the form of concentric circles propagating from the periphery to the center of the object at a propagation speed;

exciting acoustic waves in accordance with a distortion distribution generated in the surface of the object attributable to a photo-thermal effect of the interference fringes, the acoustic waves being focused to a small region in the object, a position of which region is determined by the specific acoustic speed of the object and the propagation speed of the interference fringes; and detecting the acoustic waves reflected by the small region or allowed to pass through the small region and then allowed to reach a front surface or a rear surface of the object with a probe beam so as to analyze characteristics of the material of the object.

3. A method according to claim 2, further comprising:

relatively scanning the object with respect to the parallel energy beams, the focusing energy beams, or the probe beam.

4. A method according to claim 2, wherein said detecting step comprises a substep of performing any one of an optical knife edge method, a heterodyne method and a Fabry-Pérot method.

5. An apparatus for evaluating a material of an object, the apparatus comprising:

means for generating coherent parallel energy beams and coherent focusing energy beams, said coherent parallel energy beams and said coherent focusing energy beams having different frequencies;

means for irradiating a surface of the object with the coherent parallel energy beams and the coherent focusing energy beams to excite acoustic waves focused to a small region in the object; and detecting means for the acoustic waves reflected by the small region or allowed to pass through the small region and then allowed to reach a front surface or a rear surface of the object with a probe beam so as to analyze characteristics of the material of the object.

6. An apparatus according to claim 5, wherein said detecting means detects the acoustic waves while relatively scanning the object with respect to the parallel energy beams, the focusing energy beams, or the probe beam.

7. An apparatus according to claim 5, wherein said detecting means comprises means for performing any one of an optical knife edge method, a heterodyne method and a Fabry-Pérot method.

8. A method of exciting acoustic waves comprising the following steps of:

irradiating a surface of an object having a specific acoustic speed of V with coherent focusing energy beams and coherent parallel energy beams, said coherent focusing energy beams having a wavelength of $\lambda$ and said coherent parallel energy beams and said coherent focusing energy beams having frequencies which are different from each other by f in such a manner that the parallel energy beams and the focusing energy beams overlap each other while locating a focal point of the focusing energy beams at depth d from the surface of the object which satisfies the following relation:

$$f \times \sqrt{\lambda^2 + 2\lambda d} > V$$

to form concentric interference fringes propagating toward an inside portion of the object; and exciting acoustic waves which are focused to a specific small region in the object in accordance with a distortion distribution generated on the surface of the object attributable to a photo-thermal effect of the interference fringes.

9. A method according to claim 8, wherein a depth of the small region to which the acoustic waves are focused is changed by changing focal depth d of the focusing energy beams.

10. A method according to claim 8, wherein a depth of the small region to which the acoustic waves are focused is changed by changing the frequency difference f between the focusing energy beams and the parallel energy beams.

11. A method according to claim 8, wherein the small region to which the acoustic waves are focused is shifted in the horizontal direction by changing an angle of incidence of the parallel energy beams with which the surface of the object is irradiated.

12. An apparatus for exciting acoustic waves comprising:

means for irradiating a surface of an object having a specific acoustic speed of V with coherent focusing energy beams and coherent parallel energy beams, said coherent focusing energy beams having a wavelength of $\lambda$ and said coherent parallel energy beams and said coherent focusing energy beams having frequencies which are different from each other by f in such a manner that the parallel energy beams and the focusing energy beams overlap each other while locating a focal point of the focusing energy beams at depth d from the surface of the object which satisfies the following relation:

$$f \times \sqrt{\lambda^2 + 2\lambda d} > V$$

to form concentric interference fringes propagating toward an inside portion of the object; and means for exciting acoustic waves which are focused to a specific small region in the object in accordance with a distortion distribution generated on the surface of the object attributable to a photo-thermal effect of the interference fringes; and means for changing a depth of the small region in the object to which the acoustic waves are focused.

13. An apparatus according to claim 12, wherein said depth changing means comprises a lens and a reflective member for changing the focal depth d of the focusing energy beams.

14. An apparatus according to claim 12, wherein said depth changing means comprises means for changing the frequency difference f between the focusing energy beams and the parallel energy beams.

15. An apparatus according to claim 12, wherein said depth changing means comprises means for changing an angle of incidence of the parallel energy beams with which the surface of the object is irradiated.

* * * * *